(12) United States Patent
Protsenko et al.

(10) Patent No.: US 7,416,550 B2
(45) Date of Patent: Aug. 26, 2008

(54) METHOD AND APPARATUS FOR THE CONTROL AND MONITORING OF SHAPE CHANGE IN TISSUE

(75) Inventors: Dmitry E. Protsenko, Costa Mesa, CA (US); Brian J. F. Wong, Irvine, CA (US); Guillermo Aguilar-Mendoza, Corona, CA (US); Ki-Hong Kevin Ho, San Francisco, CA (US); Sergio Diaz, Pamplona (ES)

(73) Assignee: The Regents of the University of California, Oakland, CA (US)

( * ) Notice: Subject to any disclaimer, the term of this patent is extended or adjusted under 35 U.S.C. 154(b) by 404 days.

(21) Appl. No.: 10/762,639

(22) Filed: Jan. 22, 2004

(65) Prior Publication Data

US 2004/0236320 A1  Nov. 25, 2004

Related U.S. Application Data

(60) Provisional application No. 60/442,219, filed on Jan. 24, 2003, provisional application No. 60/442,100, filed on Jan. 23, 2003, provisional application No. 60/441,292, filed on Jan. 21, 2003.

(51) Int. Cl.
    *A61B 18/12* (2006.01)
(52) U.S. Cl. .............................. 606/41; 606/32; 606/42
(58) Field of Classification Search .............. 606/27–52, 606/41, 32; 327/369
    See application file for complete search history.

(56) References Cited

U.S. PATENT DOCUMENTS

| | | | | |
|---|---|---|---|---|
| 5,904,709 | A | * | 5/1999 | Arndt et al. ................... 607/101 |
| 6,071,280 | A | * | 6/2000 | Edwards et al. ................ 606/41 |
| 6,557,559 | B1 | * | 5/2003 | Eggers et al. ................ 128/898 |
| 6,589,235 | B2 | * | 7/2003 | Wong et al. .................... 606/32 |
| 6,770,070 | B1 | * | 8/2004 | Balbierz ....................... 606/41 |

* cited by examiner

*Primary Examiner*—Roy D Gibson
(74) *Attorney, Agent, or Firm*—Daniel L. Dawes (57) ABSTRACT

A method of electroforming tissue comprises creating stress in the tissue; and causing a direct current to flow in the tissue to change the stress, strain, or intrinsic mechanical properties including shape of the tissue. Force is mechanically applied to the tissue to create external stresses or material parameters of the tissue are used to create internal stresses in the tissue by causing a current to flow in the tissue. The method further comprises the step of monitoring the stresses in the tissue and controlling the current flowing in the tissue according to the stresses therein by monitoring impedance, the optical properties, the pH, acoustic properties of the tissue, the gas formation in the tissue, the color of the tissue as caused by a chemical dye disposed therein or as caused by electroplating a material thereon.

3 Claims, 10 Drawing Sheets

FIG. 1

A : ACRYLIC BLOCK
C : CARTILAGE SPECIMEN
⬡ : SECURING SCREWS
oooo : ALUMINUM ELECTRODES

FIG. 16E

METHOD AND APPARATUS FOR THE CONTROL AND MONITORING OF SHAPE CHANGE IN TISSUE

RELATED APPLICATIONS

The present application is related to U.S. Provisional Patent Application Ser. No. 60/441,292, filed on Jan. 21, 2003, Ser. No. 60/442,219, filed on Jan. 24, 2003, and Ser. No. 60/442,100, filed on Jan. 23, 2003, which is incorporated herein by reference and to which priority is claimed pursuant to 35 USC 119.

GOVERNMENT SUPPORT

This invention was made with Government support under Grant No. DC00170, awarded by the National Institutes of Health. The Government has certain rights in this invention.

BACKGROUND OF THE INVENTION

1. Field of the Invention

The invention relates to the field of tissue reconstruction and in particular to electroforming tissue and cartilage in particular.

2. Description of the Prior Art

Cartilage serves many functional and structural roles in the head and neck, including the support of soft tissue in the ear and nose, maintenance of airway patency, phonation, and joint movement. The functional and esthetic defects in the head and neck that result from cancer surgery, trauma, or congenital malformations have led to the development of surgical techniques to reshape cartilage to recreate damaged or absent structures.

Conventional reconstructive techniques (e.g., otoplasty, rhinoplasty, tracheoplasty) involve the grafting or shape modification of autologous cartilage (harvested from the ear, nasal septum, or rib). Currently, the graft is carved, sutured, and/or morselized to recreate the shape of the absent tissue and, as a consequence, abundant normal healthy cartilage tissue is discarded. These techniques also in general require surgical exposure of the tissue to provide direct access to the graft tissue. Further manipulation of tissue in this fashion creates focal injury to the extracellular matrix. Because only a limited amount of cartilage is available from donor sites, conventional reconstructive techniques may lead to significant donor site morbidity. Similarly, some cartilaginous malformations in the head and neck are treated using surgical techniques that do not require grafting (e.g., rhinoplasty, laryngoplasty), but rather reshaping pre-existing cartilage structures in situ using the aforementioned traditional reconstructive techniques. These techniques have the same limitations as grafting techniques, and also require open/invasive (non-endoscopic) surgical approaches that frequently result in undesirable, irreversible tissue changes and complications that may require revision surgery, and possibly additional cartilage grafting.

Current reconstructive techniques include carving, morselizing, scoring, or suturing native cartilage grafts. The disadvantages of these approaches include donor site morbidity from graft harvest, waste of excess graft tissue, shape memory effects, and lack of control over warping, particularly in costal cartilage tissue.

Several alternative approaches to reshaping cartilage have been advocated, including enzymatic digestion in situ, radiofrequency (RF) reshaping, and laser cartilage reshaping. Of these approaches to changing the shape of native cartilage tissue, laser reshaping has received the most attention. In 1993, Helidonis et al. "*Laser Shaping Of Composite Cartilage Grafts*". Am J Otolaryngol 1993;14: 410-412, proposed an alternative laser assisted approach based on thermal-mediated stress relaxation to reshape cartilage. Despite clinical uses of laser technology to reshape human cartilage, this method remains investigational, and the associated biophysical changes accompanying shape change are incompletely understood.

Recently several new techniques have been developed and/or investigated including electroforming, thermoforming (laser and RF), and enzymatic reshaping. In each of these cases, the intrinsic forces in tissue which resist deformation are relieved or balanced by accelerating stress relaxation, albeit the molecular mechanisms of action may be different in each case. During the reshaping process, internal stress decreases over time, and this is the most important physical process to monitor during any shape change procedure. Internal stress measurements are very difficult to perform and require the application of strain gauge type devices to measure either stress or strain.

BRIEF SUMMARY OF THE INVENTION

As an extension of the work in our laboratory focused on cartilage reshaping, we have developed a technique that can be used to reshape cartilage tissue by combining mechanical deformation with the application of direct current (DC) electric fields. Although electrosurgery has been a fixture in surgery for over a century, the concept of tissue electromechanical reshaping (hereafter defined as "electroforming") is novel, and is based on the observation that cartilage is a piezoelectric material. Initially, we postulated that the application of DC voltage may result in redistribution of the fixed and the free charge in this tissue, leading to significant changes in tissue material properties. Composed of a network of collagen, proteoglycans, and water, the cartilage matrix is innately electronegative, and this electric charge is only partially compensated by free cations that permeate the interstitial fluid. The presence of this charge distribution generates a double layer electric field with a large electrical charge density.

Within the double-layer regions, it has been demonstrated that cations may move freely within the matrix, and these cations separate from the fixed negative charges during mechanical deformation. Based on this phenomenon of charge separation or streaming potential, we hypothesized that cations undergo reorganization when placed in an electric field.

We describe below the biophysical behavior of cartilage during electroforming by showing the degree of shape change in porcine nasal septal cartilage grafts. In particular, we evaluate the dependence of shape change on the magnitude and polarity of the applied DC voltage and application time as well as monitoring tissue temperature, internal stress and impedance and electrode deposition during this reshaping process. Characterizing the effects of applied voltage and the duration of treatment is an important step in understanding the physical processes responsible for electroforming and providing insight into how this procedure can be optimized.

This disclosure describes the process of tissue electroforming and how shape changes in cartilage can be produced by the application of direct current (DC). The dependence of shape change on voltage, application time and electrode composition is explained. In the illustrated embodiment, the investigation uses ex vivo porcine septal cartilage grafts and electromechanical cartilage deformation focused on development of a new surgical technique. To illustrate the invention uniform flat porcine nasal septal cartilage specimens were mechanically deformed between two semicircular aluminum and gold electrodes. DC current was applied to establish charge separation and electrical streaming potential. Voltage (0-6 V) and application time (0-5 minutes) were varied. Shape change was measured, and shape retention was calculated using analytic representation. The effect of the direction of applied current on shape change was evaluated by switching the polarities of electrodes and using parameters of 0 to 5.5 V and 5 minutes. Temperature during reshaping was monitored with a thermocouple, internal stress was monitored with a load cell, tissue impedance was monitored with a volt- and ampermeter and surface features were evaluated using light microscopy. Reshaped specimen demonstrated mechanical stability similar to native cartilage tissue. Shape retention and stress relaxation strongly correlated with increasing voltage and application time. Only a small current (<0.1 A) through the tissue was measured. Temperature change was less than 2° C. during electroforming, suggesting that electroforming likely results from some nonthermal mechanisms. Tissue impedance change accompanied with stress relaxation likely confirms electro-mechanical mechanism of reshaping. Surface features indicated that electrodeposition may occur depending on electrode material and magnitude of the applied voltage.

These findings demonstrate that cartilage can be reshaped through the process we have described as "electroforming" by generating intrinsic differences in charge separation with negligible heat production.

Thus the invention can be defined as a method of electroforming tissue comprising the steps of creating stress in the tissue; and applying DC voltage to the tissue. while the created stress is present to change shape of the tissue or material parameters of the tissue.

The step of applying DC voltage to the tissue causes a current to flow in the electrical circuit comprises the step of causing a direct current of a predetermined polarity to flow in the tissue or parts of the tissue to mediate the tissue.

The step of creating stress in the tissue comprises in one embodiment the step of mechanically applying force to the tissue to create external stresses applied to the tissue. In another embodiment the step of creating stress in the tissue comprises changing material parameters of the tissue to create internal stresses in the tissue by causing a current to flow in the tissue.

The method further comprises the step of monitoring the stresses in the tissue and controlling the current flowing in the tissue according to the stresses therein. The step of monitoring the stresses in the tissue comprises monitoring impedance, the optical properties, the pH, acoustic properties of the tissue, the gas formation in the tissue, the color of the tissue as caused by a chemical dye disposed therein or as caused by electroplating a material thereon.

The step of applying DC voltage to the tissue comprises the step of applying a voltage of predetermined polarity to obtain a predetermined bioeffect, such as applying pulses of voltage of the same polarity to form a DC pulse train, or applying a first sequence of pulses of voltage of the same polarity and applying a second sequence of pulses of voltage of the opposite polarity to form a complex DC pulse train with net charge cancellation when integrated over an application time.

The step of applying a voltage of predetermined polarity to obtain a predetermined bioeffect comprises the step of flowing current from a positive electrode to obtain tissue compression in the proximity of the positive electrode. Similarly, the step of applying a voltage of predetermined polarity to obtain a predetermined bioeffect comprises flowing current from a negative electrode to obtain tissue lengthening in the proximity of the negative electrode.

The step of creating stress in the tissue comprises creating tension, compression shear or a combination thereof in the tissue.

The step of causing a current to flow in the tissue comprises applying a DC voltage for a predetermined application time across two paired conductive elements in contact with the tissue, such as by placing a solid conductive element in contact with the tissue, including solid conductive elements composed of metals or conductive polymers, or by placing a conductive gel or solution in contact with the tissue. In another embodiment the tissue is penetrated or point-contacted with at least one conductive needle or with an array of point contacts.

The step of creating stress in the tissue and causing a current to flow in the tissue comprises the step of contacting the tissue with a pair of curved electrodes, which may include contact with a sharply angled electrode or a smoothly angled electrode.

The invention can be further defined as a method of electroforming cartilage comprising the steps of mechanically inducing a predetermined desired shape of the cartilage; applying electrical energy to cartilage to cause electrolytic conduction of current through the cartilage for a predetermined application time while mechanically maintaining the predetermined desired shape; and ceasing the application of electrolytic conduction of current through the cartilage and freeing the cartilage from mechanical shaping. The electrolytic conduction of current is limited to provide a substantially nonthermal method. The step of applying electrical energy to cartilage causes cartilage shaping to occur through electroplating, electrophoresis, protein denaturation, transitions of bound to free water, water transport, hydrolysis, pH change, electrochemical reactions, local mineralization or a combination thereof.

The step of applying electrical energy to cartilage is by means of a DC voltage being applied across a pair of electrodes, which causes cartilage shaping to occur through molecular dissociation of the components of the cartilage in the vicinity of the electrodes and subsequent chemical reactions of dissociation products which in turn induces volumetric molecular reorganization within the tissue.

The invention further includes apparatus through which the above methods may be performed.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 13b is a side cross sectional view taken through line 13b-13b of FIG. 13a.

FIG. 14b shows the positioning of a jig or electrode in contact with the cartilage.

FIGS. 15a-15c are bottom plan views showing the anatomical position of the medial and lateral cura in the nose. FIG. 15a shows the nose before treatment, FIG. 15b after treatment and FIG. 15c illustrates the treatment.

FIGS. 16a-16e illustrate the application of the invention to the thyroid cartilage.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The present invention may be useful for tissue mediation which is cosmetic, reconstructive or corrective, for example in otorhinolaryngology, orthopedics, cosmetic and plastic surgery procedures in the head and neck. In addition the invention may be applied to shaping or changing the material parameters of any soft or cartilaginous tissue, including but not limited to cartilage, tendon, ligament, dermis, skin, muscle, fascia, nerve tissue, gastrointestinal tissue, corneas, ear drums, or larynx tissues. The preferred targets include all forms of cartilage in the body in all sites, tendon, ligament, cornea, tympanic membrane. However, muscle, nerve, fascia, dermis, skin, intestinal and respiratory tract tissue are also included. For example, the present invention is particularly useful for shaping cartilaginous tissue, such as the cartilage within the nose that is sculpted during rhinoplasty procedures. The shaping is to be broadly understood to include morphological changes due to applied or expressed tension, compression or shear forces on the tissue. Electromechanical reshaping of cartilage will lead to broad changes in the practice of plastic and reconstructive surgery. The invention is believed to be efficacious in any tissue having piezoelectric characteristics. Thus, while cartilage is demonstrably responsive to the methodology of the invention, application to other tissues are expressly contemplated as well. For example, to the extent that the elastin or the elastic component in skin or muscle has piezoelectric characteristics, an applied current or electric field in compressed tissue may result in the reduction in sagging and thinning of skin or muscle tissues to a degree effective for general use in plastic surgery.

Figure 1:
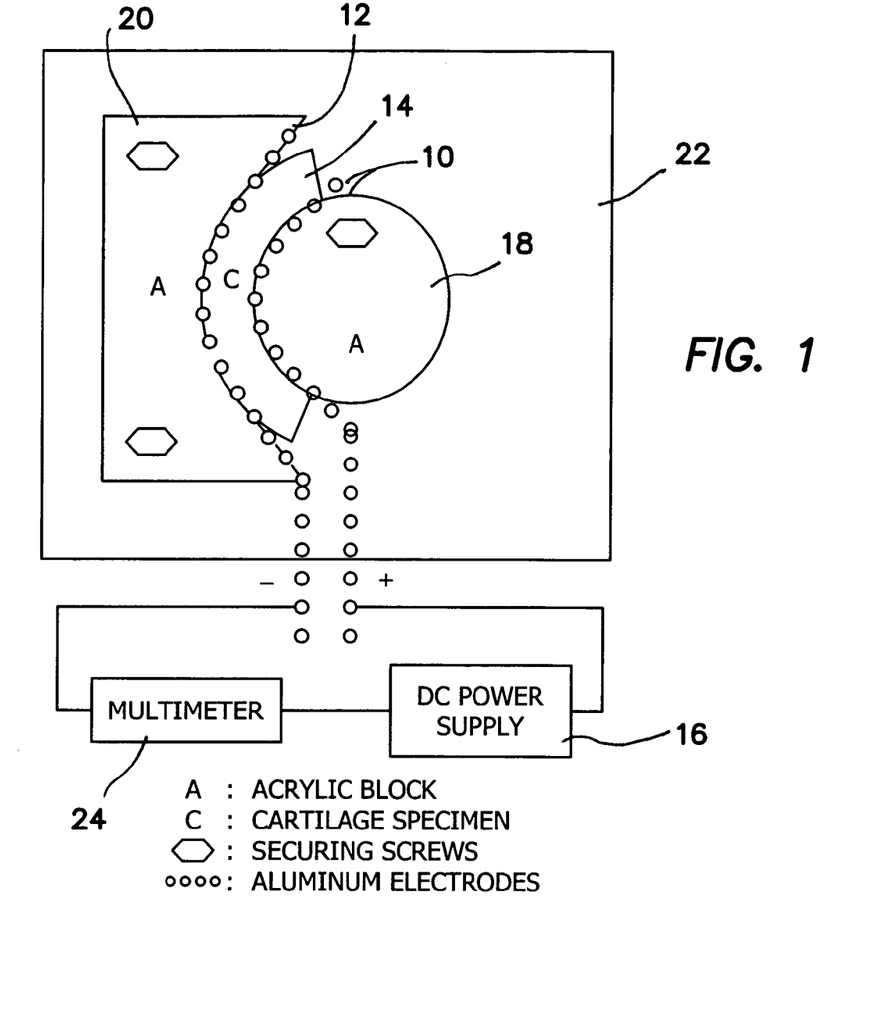
FIG. 1 is a simplified diagram of the illustrated embodiment in which the principle of the invention is proven and explained.

The invention can be used to alter the morphology and/or mechanical properties of tissue without cutting or suturing to relieve and/or balance the intrinsic elastic forces that resist deformation. When electrical energy is applied to the electrodes 10, 12 as depicted in FIG. 1, the tissue 14 is modified via molecular dissociation of its components, which in turn activate a structural reorganization within the tissue matrix, although other mechanism may be responsible as well. During this process, mechanically deformed tissue 14 can acquire new shapes that are permanently retained after treatment. Tissue modification can thus be achieved using minimally invasive techniques, with less morbidity than traditional reconstructive procedures. This is a substantial improvement over classic reconstructive surgeries that require general anesthesia, increased physician time, and the loss of several days work on the part of the patient. In addition, the invention uses inexpensive and readily available technology. Other tissues beside hyaline, fibro and elastic cartilage may be treated with this technique and include, but are not limited to, ligament, tendon, spinal tissue, nerves, muscle, skin, and intestines.

The invention provides a method for selectively applying electrical energy to tissue in order to modify its shape and/or biomechanical properties. As diagrammatically illustrated in FIG. 1 the method is comprised of the steps of applying electrical energy to two or more active electrodes 10, 12 that are in contact directly or indirectly with tissue 14 to mechanically deform the tissue 14. A voltage difference (or current) from source 16 is applied between the two electrodes 10, 12 to modify the target tissue, organ, or body structure 14. When applying a voltage between the active and return electrodes 10, 12, electrolytic conduction is established through the tissue 14 inducing chemical reactions to take place as ions in the tissue 14 come into contact with the electrodes 10, 12, though several other mechanisms are possible including electroplating, electrophoresis, and protein denaturation.

The electrodes 10, 12 are positioned close together to ensure that the return current flows directly from the active electrode 10 to the return electrode 12. Current flow is controlled to avoid excessive tissue heating due to high current density between the electrode 10, 12 and the tissue 14. The tissue 14 is modified via molecular dissociation of its components in the vicinity of the electrode 10, 12, which in turn induces volumetric molecular reorganization within the tissue matrix, although other physical mechanism may be responsible for this effect as well. During this process tissue 14 can acquire a new morphology that is permanently retained after treatment.

In the illustrated embodiment and to illustrate the principle of the invention, porcine nasal septal cartilages were harvested from freshly killed pigs' crania obtained from a local abattoir (Clougherty Packing Company, Vernon, Calif.). Only the cranial part of the septal cartilage was used for experimentation because previous studies in our laboratory have shown that there are regional variations in biochemical, cellular, and mechanical properties in the porcine septum along the cranial—(near the nasopharynx) caudal (near the nares) axis. Cartilage grafts from each septal cartilage were obtained and cut into uniform rectangular slabs (16×5×2 mm) using a custom guillotine microtome. In human usage the cartilage reshaping may be performed either in vivo or ex vivo followed by grafting.

Before electroforming, cartilage specimens 14 were sandwiched between two semicircular aluminum electrodes 10, 12 mounted or glued on jigs 18, 20 comprised of acrylic blocks secured by screws to an acrylic platform 22 as shown in FIG. 1. The radius of curvature of the two jigs 18 and 20 were 8 mm and 11.5 mm, respectively. Aluminum was selected as the electrode material because of its malleability, low cost, and electrical conductivity. Leads from a DC power supply 16 (Model PPS-2322, Amrel, Arcadia, Calif.) were connected to the electrodes 10, 12 to establish charge separation and establish the electrical streaming potential. As illustrated in FIG. 1, the inner and the outer curvatures of the specimen were connected to the anode 10 (positive) and cathode 12 (negative), respectively. The applied current was measured and monitored using a multimeter 24 in series with electrodes 10, 12 (2001, Keithley, Cleveland, Ohio) to avoid excessive resistive heating caused by a high current density between electrodes.

It is to be expressly understood that the mechanical means for applying the external stress may be comprised of any type of conductive element, such as metals, conductive polymers or conductive gels or electrolytic solutions carried on rigid or resilient carriers. Jigs 18, 20 may have any geometry that is desired including curved, flat, sharply or smoothly angled. In addition to have surface contact electrodes such as shown in FIG. 1, the electrodes may be one or more conductive needles which provide a point pressure contact or actual penetration into the tissue. In the case of one or both electrodes of the pair being in needle form, an array of microneedles may be employed and applied with varying voltages, so that like an ink jet printer, any two dimensional pattern of voltages on any shaped surface could be provided. In addition, if desired, a plurality of needle electrodes of one polarity may be provided mixed or arranged in a complex array of needles of the opposite polarity, or in a plurality of isolated through-holes defined in a conductive surface provided with the opposite polarity.

Voltage was varied from 0 V to 3.5 V for a set application time of 5 minutes. Likewise, the effect of application time on shape change was studied by varying application time from 1 to 6 minutes for four different voltages (1 V, 1.5 V, 2 V, 2.5 V). To study the effect of applied current direction, the polarities of the electrodes were switched (inner curvature to negative electrode), using parameters of 0 to 5.5 V and 5 minutes. Control specimens underwent identical bending procedures without the application of voltage, thus allowing determination of the effect of mechanical deformation on shape change alone.

During electroforming, surface temperature was measured using an insulated thermocouple and a cold-junction compensator (not shown) (HH509R, Omega Engineering, Stamford, Conn.) placed between the tissue specimen 14 and electrode 10, 12 to determine whether any temperature rise accompanied this process. Immediately after electroforming, specimens 14 and the securing jigs 18, 20 were immersed in a saline solution at ambient temperatures for 15 minutes in accord with protocols established for laser reshaping studies. Specimens 14 were then removed from the jigs 18, 20, photographed, and the distance between the two ends of specimen 14 was measured by a digital electronic caliper (CD-6_CS, Mitutoyo Corp, Japan).

The specimen deformation or shape change is described in terms of the bend angle. The bend angle was calculated using a model that assumes that specimen shape approximates an arc segment of a circle. The model is based on the following equation:

$$L = [2Li \sin(\theta_{expt}/2)]/\theta_{expt}$$

where L is the distance between the ends of the bent sample, Li is the initial length of the sample before deformation, and $\theta_{expt}$ is the experimental bend angle in radians numerically determined by solving the above equation using the "goal seek function" in Excel (Microsoft Corporation, Redmond, Wash.). The maximal bend angle $\theta_{max}$ was calculated by measuring the linear distance between the two ends of the specimen while it was still secured to the jigs 18, 20. The extent of shape retention was determined through normalizing $\theta_{expt}$ by the maximal bend angle $\theta_{max}$:

$$\text{Shape Retention} = \theta_{expt}/\theta_{max}$$

For the given reshaping jig and specimen dimensions used in this study, $\theta_{max}$ was within the range of 2.76 to 2.88 radians. In addition, cartilage surfaces were inspected using a high-power light microscope to ascertain whether any surface feature changes such as electrodeposition occurred.

Figure 2A:
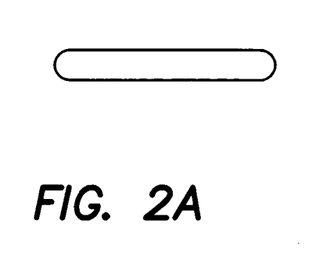
FIG. 2A is a photograph of a side view of unshaped cartilage.
Figure 2B:
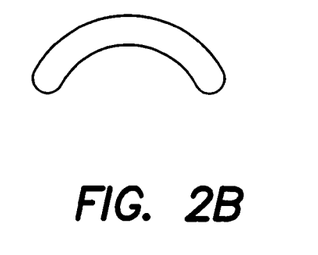
FIG. 2B is a photograph of a side view of shaped cartilage according to the invention.
Figure 3:
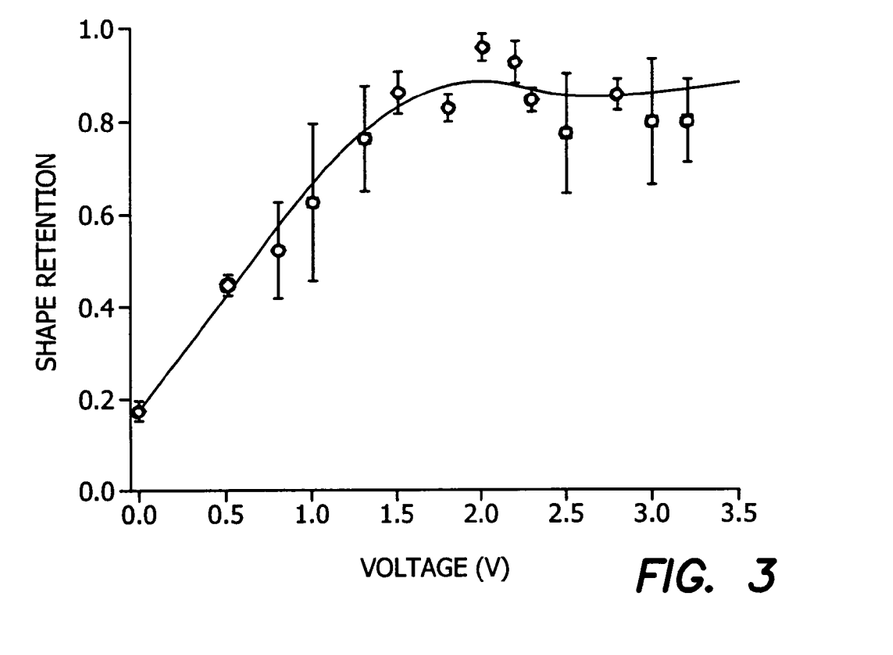
FIG. 3 is a graph of shape retention as a function of applied voltage.
Figure 4:
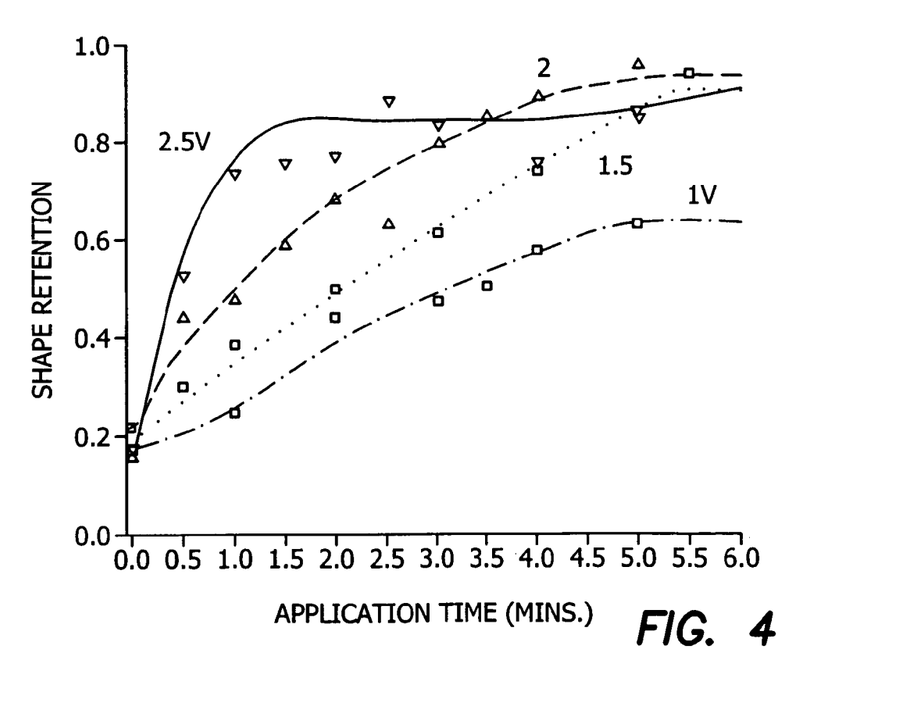
FIG. 4 is a graph of shape retention as a function of application time using four different applied voltages.

A photographic montage of cartilage specimen before and after electroforming is shown in FIGS. 2A and 2B respectively. FIGS. 3 and 4 are graphs of shape retention as a function of voltage and as a function of application time, which illustrate the effect of voltage and application time on shape retention, respectively. FIG. 3 demonstrates that degree of shape retention increases gradually with voltage, reaching a plateau value of approximately 0.84 at about 1.5 V, which represents an empirical threshold for electroforming using the present apparatus and specimen size. Values were averaged for each treatment group with error bars representing the standard error of measurement.

A similar pattern is observed when shape retention is evaluated as function of increasing voltage application time as shown in FIG. 4. With each of the four voltage studies (1 V, 1.5 V, 2 V, 2.5 V), the minimum application time required to establish near-maximal shape retention were approximately 5, 5, 4, and 1.5 minutes, respectively.

Figure 5:
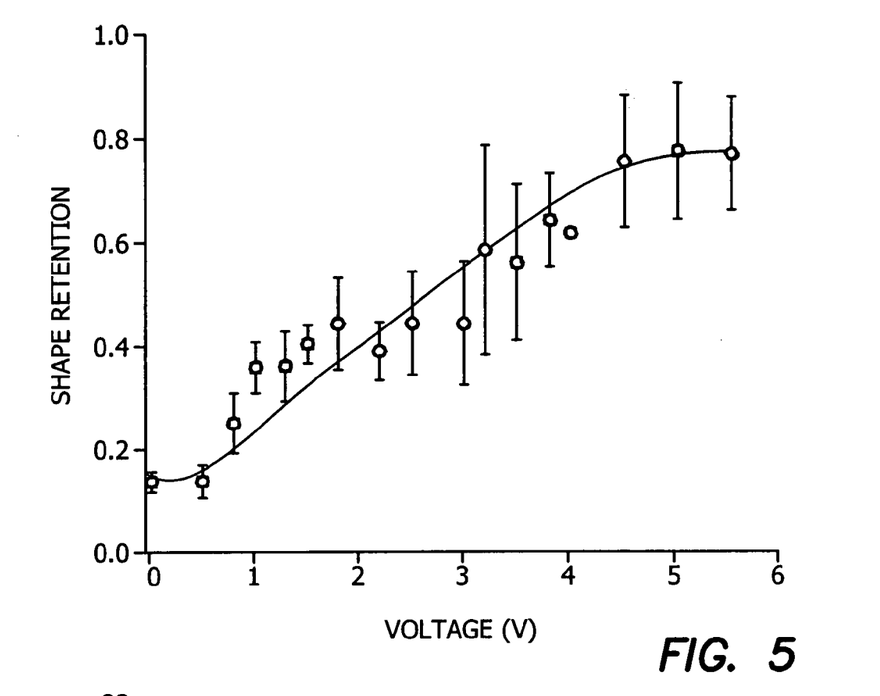
FIG. 5 is a graph of shape retention as a function of application time applied voltage with polarities of the voltage reversed as compared to FIGS. 3 and 4.

FIG. 5 is a graph of shape retention as a function of voltage, which depicts the dependence of shape retention on electric field polarity (negative electrode to the inner curvature). The threshold value (approximately 4.5 V) was significantly higher than that (1.5 V) of the experimental protocol, as shown in FIG. 3.

Figure 6:
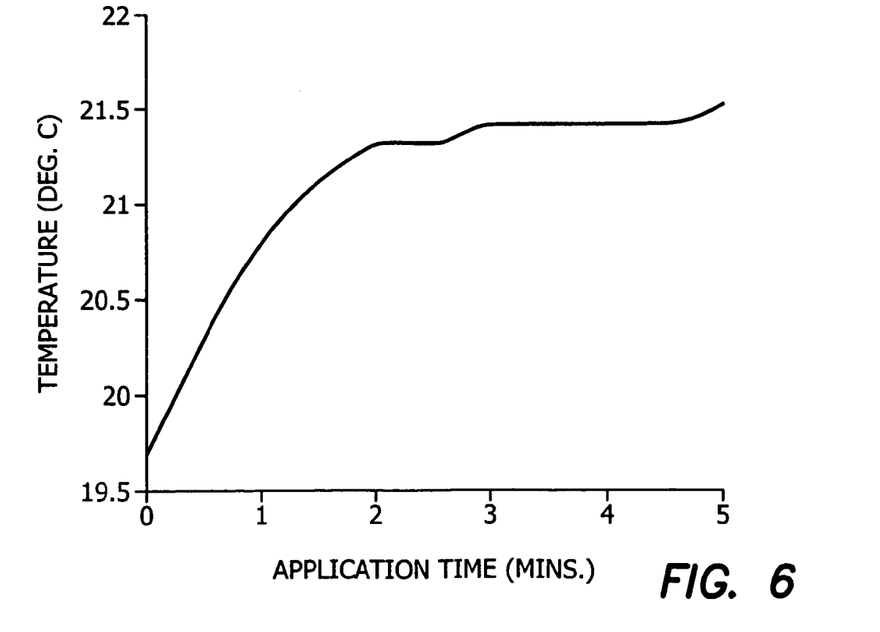
FIG. 6 is a graph of temperature as a function of application time when applying 3.5 volts.

A representative plot of surface temperature during reshaping is depicted in FIG. 6, which is a graph of temperature as a function of application time. During electroforming, surface temperature increased slowly, albeit with temperature rise of less than 2° C. after 5 minutes of electroforming at 3.5 V. During electroforming, white foam formation (small bubbles) was observed after approximately 10 seconds of voltage application. No foam generation occurred when voltages were less than 1 V. Applied current measurements were within the range of 0 to 12 mA. After electroforming and rehydration, no apparent change in dimensions or surface texture was observed. There was no char formation or any other obvious evidence of tissue injury on visual inspection. Microscopic examinations revealed minimal gray colored electrodeposition on specimen under the experimental conditions (0-3.5 V). Substantial specimen shrinkage and dark electrodeposition that likely represents electrochemical deposition of aluminum ions were observed on the specimen surface when examined under light microscopy, but only when voltage exceeded 4 V. Several reshaped specimens 14 (removed from the jigs 18, 20) were stored in saline solution (4° C.) for 24 hours, and the resulting shape retention was found to be approximately 80% to 90% of the original values measured immediately after rehydration.

Electroforming is a novel technique that can be used to reshape cartilage. Our motivation for studying cartilage electroforming was based on a number of advantages that electroforming has over other methods of cartilage reshaping including the following: 1) it is readily available at low cost; 2) it is technically simple and can conceivably be performed using a battery power source; and 3) the current can be easily controlled to avoid thermal injury, which may occur in other procedures such as laser and RF-mediated reshaping.

Our results illustrate that cartilage can undergo significant shape change by way of electroforming, and we have correlated this effect with applied voltage, application time, and electric field polarity. The experiments that focused on examining the effect of application time on shape change were performed using four different voltages to demonstrate another correlation: the time dependence (minimum time required to reach maximal reshaping) of this process. As shown in FIG. 4, for higher voltages, shorter application times are required to reach maximal shape change.

Given the trends established in this study, further analysis using larger parameter sizes will likely provide additional information on the combined effects and relative contributions of voltage and application time on shape retention and will facilitate the development of a rigorous model to describe this behavior. In addition, a memory effect was observed in these studies, as illustrated by the slight decrease in shape retention after 24 hours. Therefore, clinical implementation of this technique will likely require "overbending" of the cartilage graft to compensate for this effect. Because shape memory, like shape retention, varies with spatial location of cartilage and with the time interval allowed for the release of interlocked forces (native stress relaxation), future studies using longer observation periods will be crucial in determining the degree of overcorrection needed for achieving the desired clinical result.

The assessment of actual shape change using closed form analysis or numerical solutions is difficult and has prompted our use of the simple circle model to estimate shape change using easily measured linear dimensions. The jigs 18, 20 were carefully designed so that the inner and outer surfaces of the specimen 14 were in close contact to the rigid semicircular electrodes 10, 12. However, a variation in the maximal bend angle $\theta_{max}$ (2.76-2.88 radians) was introduced by the slight differences in specimen dimensions (primarily thickness) and the pressure exerted during mechanical deformation by the securing screw assembly. To compensate for this variation, shape retention, instead of shape change, was calculated by normalizing the final shape acquired after rehydration by the initial secured shape before electroforming. The accuracy of linear measurements was further enhanced by the use of a digital electronic caliper.

As shown in FIG. 6, surface temperature rose slightly from 19.7° C. (ambient) to 21.5° C. after 5 minutes voltage application (3.5 V), an increase of 1.8° C. Other temperature measurements were made using voltages lower than 3.5 V, and the changes in temperature over a 5-minute time span were less than 1.8° C. However, when voltage was raised to 20 V, significant heating was observed. This is not surprising because the corresponding increase in current (I) (from less than 0.1 A at 3.5 V to about 1 A at 20 V) leads to more than a 100-fold increase in power (power=$I^2 \times R$, where resistance R stays relatively constant in this case). In this study, temperature measurements have shown that very little heat is generated during this process when voltage is low and the resistance of the cartilage matrix is large (>1 k$\Omega$). Therefore, unlike RF and laser cartilage reshaping, shape change after electroforming likely results from some nonthermal mechanisms.

Although the molecular events that accompany electroforming are not known, on the basis of the results of this study and previous investigations on laser cartilage reshaping, we propose several mechanisms. The first mechanism is that electroforming results in the loss of water through hydrolysis, an electrolytic reaction that transforms water into free hydrogen and oxygen molecules. Hydrogen ions are reduced to form hydrogen gas at the cathode. At the same time, hydroxide ions are oxidized to produce oxygen gas at the anode. The observation of foam-bubble formation combined with a lack of significant temperature rise at the interface between the cartilage and the electrodes while current is supplied supports this hypothesis. It is well known that water content greatly influences the biomechanical properties of cartilage because the mechanical properties of this tissue result from the interaction of water molecules, cations $Na^+$ and $Ca^{2+}$), and negatively charged macromolecules (proteoglycan, collagen). It is believed that internal stress reduction during laser reshaping is caused by a bound-to-free transition of water molecules in the matrix; water loss produced by hydrolysis may produce the same changes in the matrix, leading to accelerated mechanical stress relaxation. This mechanism is compatible with our macroscopic observations, which have shown the dependence of shape change on voltage and application time. An increase in voltage creates a stronger electric field that in turn accelerates hydrolysis, thus enhancing shape change. Likewise, an increase in application time allows further loss of water from the cartilage matrix, leading to greater reshaping.

A second possible mechanism is that protein electrophoresis occurs during electroforming. When cartilage specimen is bent into a semicircular arc, the inner and outer curvatures of the specimen undergo compression increase in stress) and expansion (decrease in stress), respectively. Because the distribution of proteoglycan is the major determinant of the internal stress within cartilage matrix, a bent specimen has a higher density of proteoglycan molecules at the inner curvature and the lower density at the outer curvature. When voltage is applied, migration of negatively charged proteoglycan molecules toward the positive electrode increases the density of proteoglycan at the inner curvature, thus stabilizing the bent configuration. When the polarities are reversed, there are less proteoglycan molecules at the inner curvature, resulting in less shape change for a given voltage as illustrated in FIG. 5. In conventional gel electrophoresis, where distance traveled by protein fragments is dependent on both applied voltage and running time, a higher voltage or longer application time will likely result in a larger proteoglycan accumulation at the inner curvature and therefore greater shape change.

The third mechanism involves the alteration in intrinsic molecular structure within cartilage matrix, including depolymerization of proteoglycan molecules or collagen molecules, disruption of bonds between the collagen and proteoglycan subsystems, and bound-to-free water transition. When triggered by the application of electric field, these processes could lead to temporary disruption and formation of bonds, alteration of internal stress, and permanent molecular reorganization.

Our initial consideration of aluminum as the electrode material was mainly for practical reasons: 1) low cost and ready availability, 2) high conductivity, and 3) high malleability. However, one concern with aluminum is that it has a low standard electrode (reduction) potential (−1.7 V) among metals with high conductivity. The standard electrode potential correlates with the likelihood of a metal to undergo oxidation and electrodeposition. A low potential material like aluminum would produce more electrodeposition than metals with higher standard electrode potentials such as silver (0.8 V) and gold (1.5 V). Although the effect of electrodeposition on cartilage reshaping is not fully understood, it is unlikely that electrodeposition plays a primary role in shape change because our observations indicate that substantial shape change can occur with minimal deposition when low voltages such as 2 V are used. Therefore, we opted not to use gold or silver electrodes in this study so as to minimize expenses. There are reasons, however, to believe that electrodeposition exerts a complementary effect on cartilage reshaping. One possible mechanism is that metal deposition changes the extrinsic or intrinsic structure of the cartilage matrix, providing stabilization to the bent configuration specified by the jig. Few studies have focused on the effect of electrodeposition on tissue, yet there are several therapeutic treatments based on the use of metals, such as the use of gold injection therapy for early active rheumatoid arthritis and other synovial inflammatory diseases. Studies on the use of other electrode materials and viability of specimens are currently underway to evaluate the values and optimize the process of cartilage electroforming.

This disclosure also contemplates a new means of monitoring the "shape change" or "material parameter change" process during tissue or cartilage mediation or reshaping. The fundamental monitoring principle is that in biologic tissues held or maintained in deformation or under a constant strain, the electrical impedance of the tissue can be measured and be used as a feedback control in the reshaping or electroforming process. While demonstrated here in cartilage the technique has broad application to other tissues and can be used to monitor creep as well as stress relaxation.

Figure 7A:
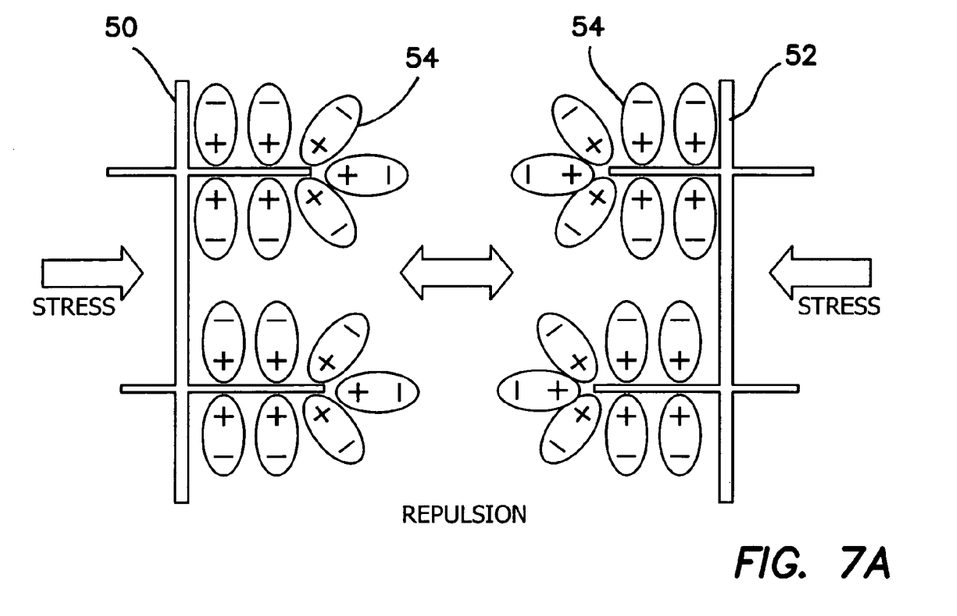
FIGS. 7A, 7B and 7C are diagrams with illustrate a model of the electroforming biomechanism.
Figure 7B:
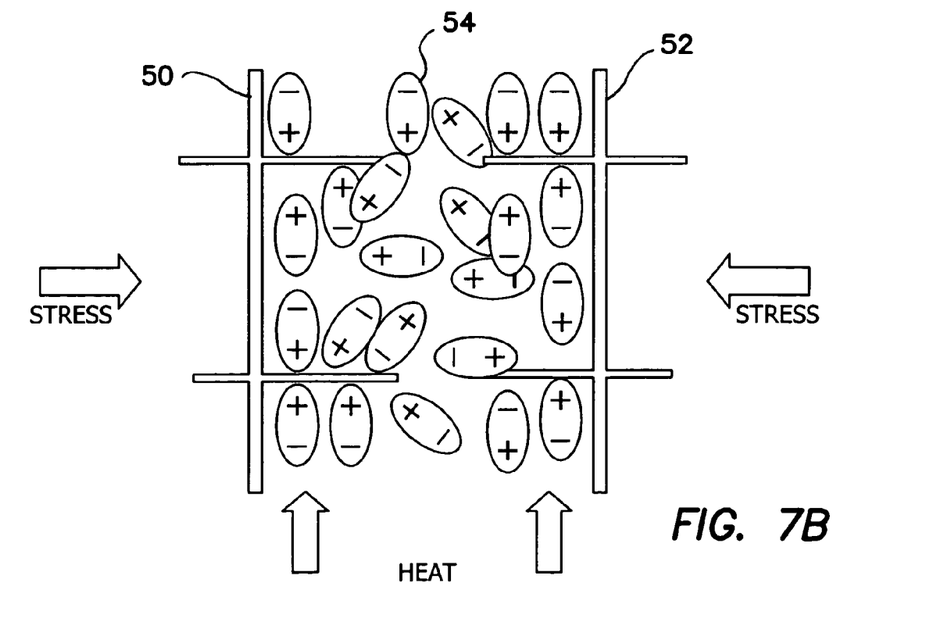
Figure 7C:
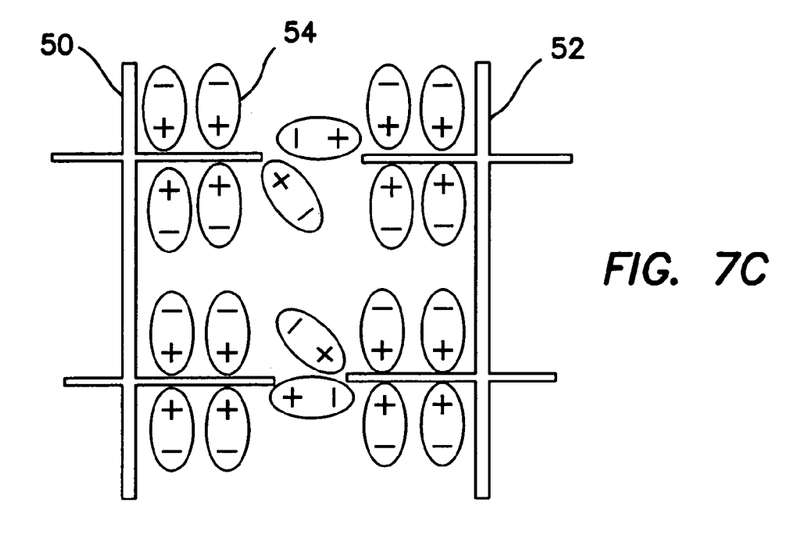

The actual impedance signal can be analyzed in the time and frequency domain and be fit to either analytic or empirical equations to optimize the process of the invention as well. Simple embodiments of such monitoring methods include the use of measuring electrical impedance and analyzing phase and power spectra. Another approach is to normalize real time measurements of impedance by the initial impedance prior to intervention. In electroforming experiments, impedance measurements are correlated with both stress relaxation and degree of shape or material parameter change produced. Electrical methods are very inexpensive and provide data which corresponds to bulk changes in material properties. They may be more sensitive to picking up subtle changes in tissue as well. FIG. 7A is a diagrammatic model which illustrates one possible biomechanism. The tissue matrix is comprised of collagen fibers 50 and proteoglycans 52 each with hydrated polar water films. Under stress the hydrated collagen fibers 50 and proteoglycans 52 are forced together as illustrated in FIG. 7B. When the charges are redistributed under the influence of electrical current flowing through the tissue matrix, stress relaxation occurs as a result of redistribution of electric charge between fixed charge associated with the proteoglycan groups attached to the collagen matrix and free charge associated with the cartilage ionic solution component as depicted in FIG. 7C. This redistribution of electric charge causes an alteration of the cartilage electric impedance and is used according to the invention as a measure of the physical state of the cartilage during reshaping.

Figure 8A:
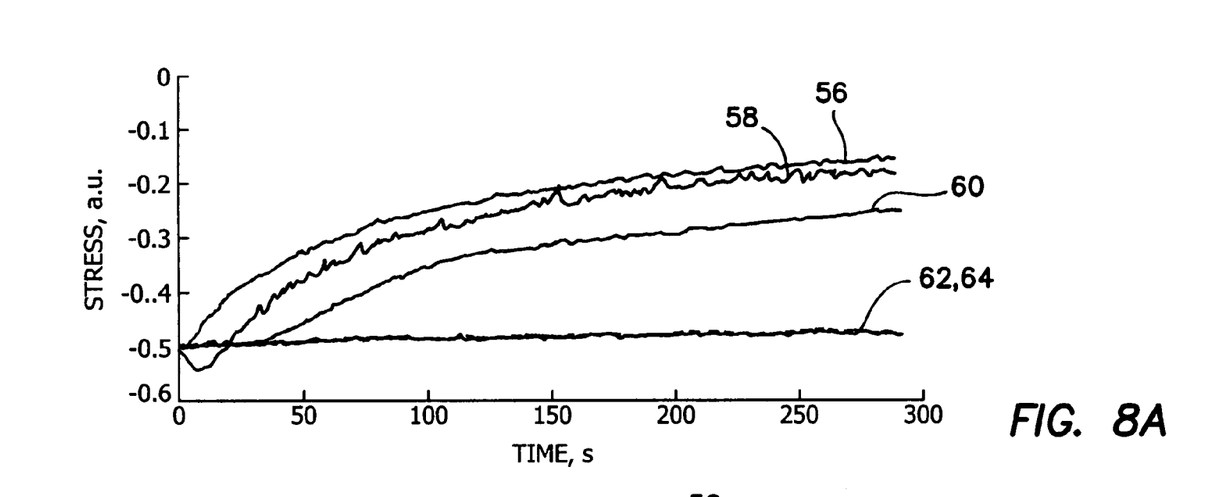
FIGS. 8A and 8B are graphs of resistance and stress as a function of time at different electroforming voltages.
Figure 8B:
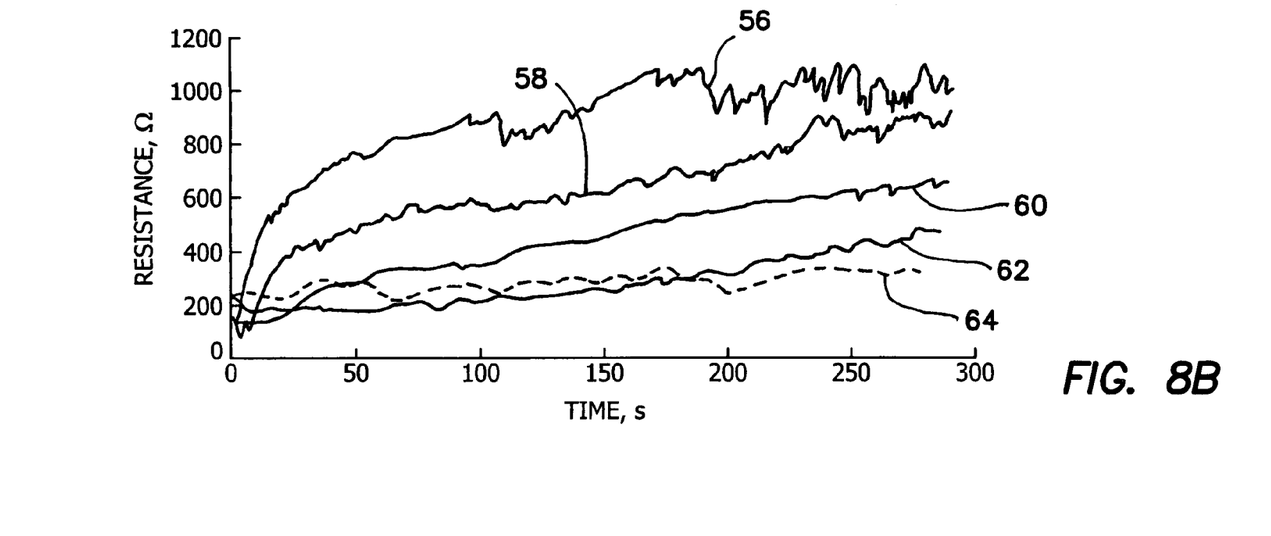
Figure 9:
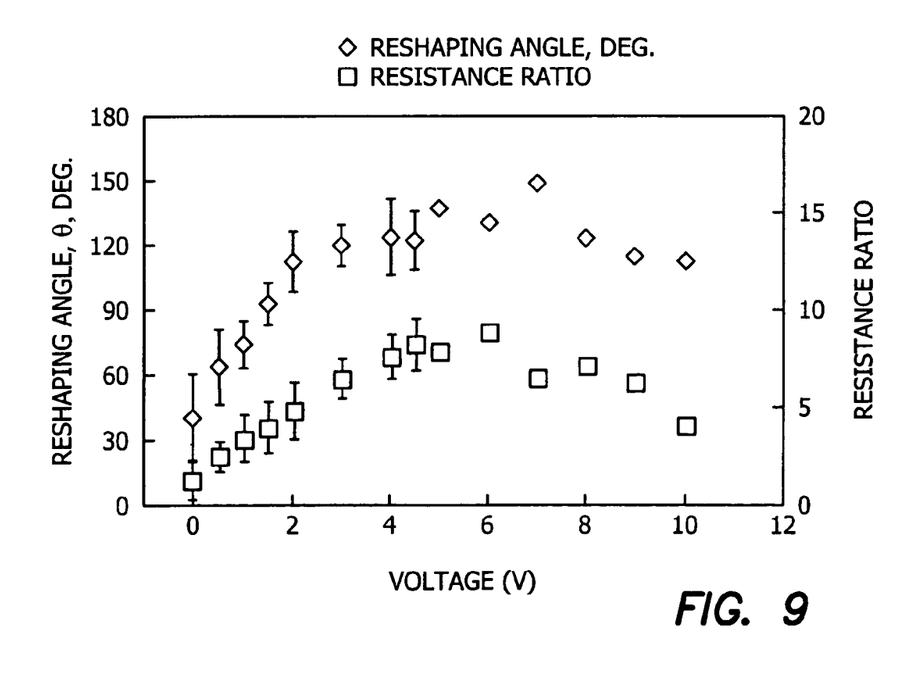
FIG. 9 is a graph of the maximum reshaping angle and normalized resistance as a function of electroforming voltage.

FIG. 8A is a graph of stress in rabbit cartilage using an Al electrode pair as in FIG. 1 as a function of time for four different electroforming voltages, 8, 4, 2 and 0.5 volts, shown as graphs 56, 58, 60 and 62 respectively and a control 64 shown in dotted outline. FIG. 8B is a graph of resistance in rabbit cartilage at the same four electroforming voltages and control as a function of time. It is clear that resistance correlates with stress relaxation as a function of time for viable voltage levels. FIG. 9 is a graph of the maximum reshaping angle and normalized final resistance, $R_{after}/R_{before}$, in rabbit cartilage that can be achieved as a function of electroforming voltage. Again it is clear that the normalized final resistance, $R_{after}/R_{before}$, correlates with the maximum reshaping angle in cartilage. Although it is not entirely understood, it is believed that the mechanism of electroforming and impedance change is due to a thermal-like detachment and reattachment of water molecules from the proteoglycans and to a pH mediated dissociation of water molecules and electrochemical reactions at the electrodes, which creates a disassociation current component and an ionic current component.

Figures 10A, 10B, 10C:
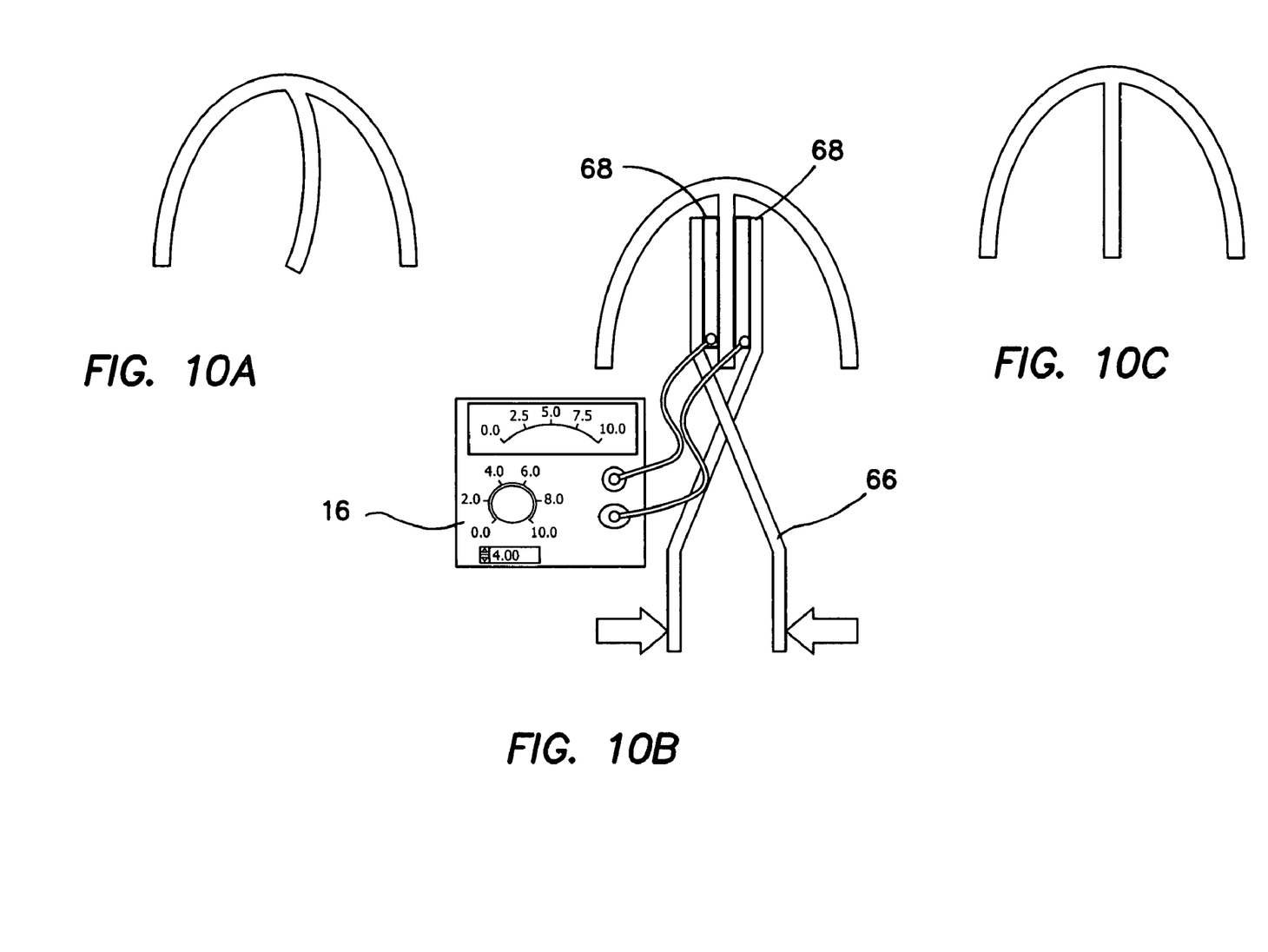
FIG. 10 is a simplified view of a surgical instrument for shaping the cartilage in the septum of a nose according to the invention.

In a surgical context as shown in FIG. 10 an instrument can be devised in which the two electrodes are brought to bear on the tissue site either in the form of pressure electrodes or penetrating electrodes or both. The electrode pair 68 may, for example, be mounted on and electrically isolated on a pair of tongs 66 coupled to a current or voltage source 16 and comprise a mold. The surgeon then brings the instrument 66 into contact with at least one of the molded surfaces of the tissue to be reshaped, creates the stress, and applies an effective voltage for effective time to obtain the molded shape desired. The electrodes 68 may be subdivided into multiple pieces so that there is an array of small plate electrodes or a needle array as described above.

For example, where only one surface of the cartilage or tissue is accessible, a molded electrode surface is brought to bear against the accessible tissue surface to provide pressure or stress in the tissue, namely to indent the surface, and one or more needles are inserted to effectively form the opposing electrode across the indented tissue layer to be reshaped. The tissue will tend to permanently bend to conform to the molded electrode.

Figure 11:
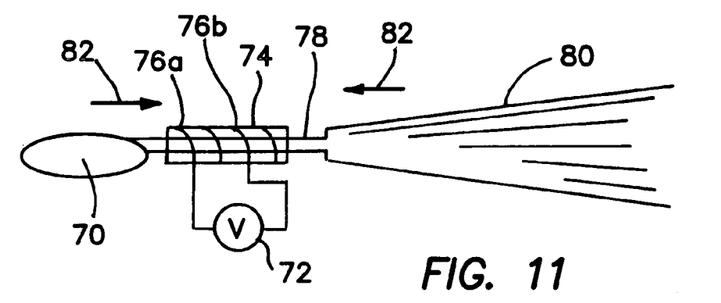
FIG. 11 is a side plan view of a diagram showing a jig with wire electrodes being applied to a tendon under compression to shorten it.

FIG. 11 is a simplified diagram of an application of the invention to shorten or gather tendon 78 attached between a bone 70 and muscle 80. A split cylindrical jig 74 is disposed around a tendon 78 and applies by mechanical means (not shown) a compressive force symbolized by arrows 82 in FIG. 11 shortening and thickening tendon 78. For example, jig 74 may have end grips or pins that attach to tendon 78 which clamps or pins can be compressed toward each other such as by movement of a pin in a slot or by collapse of telescopic portions of cylindrical jig 74. A potential from voltage source 72 is applied to two sets of helically interlaced electrodes 76a and 76b, which in the illustrated embodiment are alternate windings or helical strips on or in form 78, insulated from or in electrical contact with tendon 78. Electrodes 76a and 76b may have any physical form or pattern desired other than two sets of helically interlaced electrodes, including forms as described in the applications below.

Figure 12A:
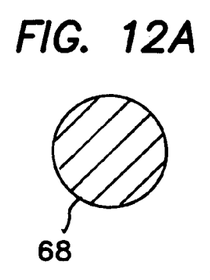
FIGS. 12a-12d are plan views of jigs carrying a variety of different forms of electrodes in form of a continuous sheet, or an array of dots, strips or needles.
Figure 12B:
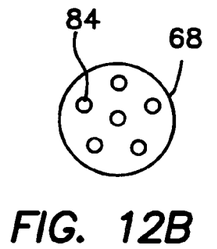
Figure 12C:
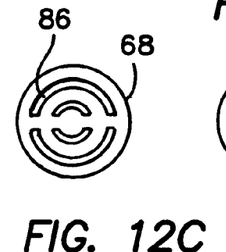
Figure 12D:
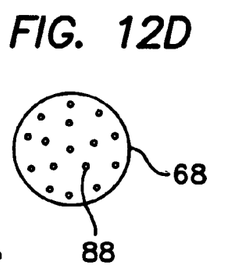

FIG. 10 diagrammatically illustrates a surgical tool for use with nasal cartilage in which the configuration of electrodes 68 assume different topologies. For example, FIG. 12a is a plan view in which electrode 68 is a uniformly conducting, flat or curved sheet, here shown as having a circular plan, but any geometric or free form shape could be employed for the plan outline. FIG. 12b illustrates electrode 68 being provided with an array of dots 84 either on a flat or curved, conducting or insulated base. Dots 84 may be coupled in common to one potential or distributed by appropriate wiring to opposing potentials or any potential pattern desired. In the preferred embodiment FIG. 12c shows an array of strip electrodes 86 on the base, which may be formed into any geometric array and again arbitrarily connected to potential values. FIG. 12d shows a plurality of needles 88 as the electrodes, which may provide concentrated points of pressure contact with the cartilage or may actually penetrate the cartilage. Again needles 88 may be formed into any geometric array and arbitrarily connected to potential values.

Figure 13A:
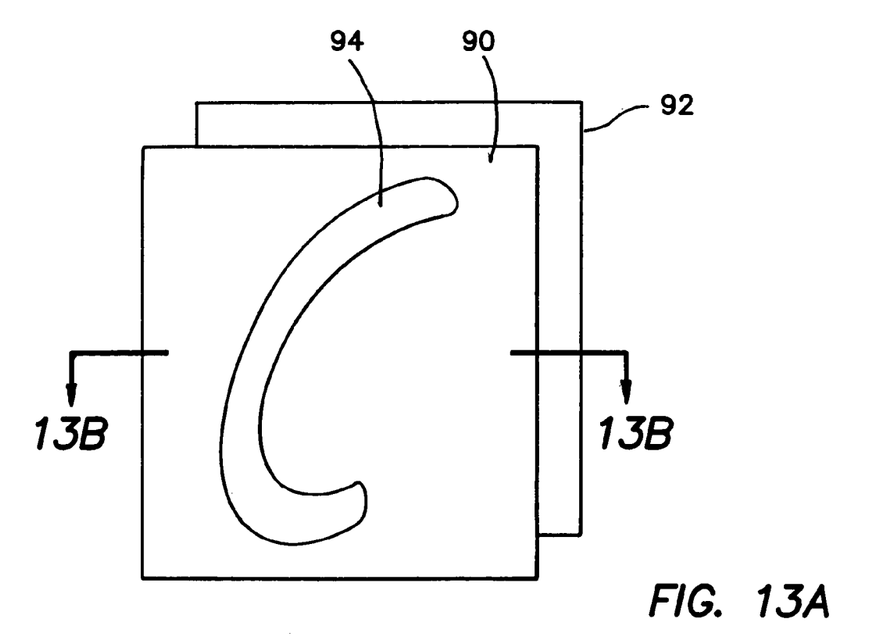
FIG. 13a is a perspective view of a pair of templates used for electroforming cartilage for the ear.
Figure 13B:
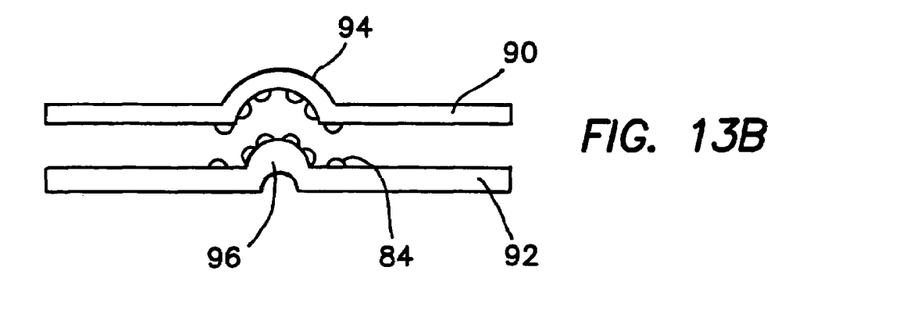

FIG. 13a is a diagram which illustrates another embodiment in which cartilage in or from the ear is electroformed. FIG. 13a is a perspective view where the electrodes comprise a template between which the cartilage is placed either ex vivo or in vivo. When used ex vivo the cartilage can be harvested from a cadaver or the patient, electroformed and then implanted. A predetermined shape for the cartilage is defined by mold 94 formed in template half 90 as shown in FIG. 13a and by a mating form 96 in template half 92 as shown in FIG. 13b, which is a side cross sectional view taken through lines 13b-13b in FIG. 13a. In this embodiment dots 84, shown in greatly enlarged scale, are provided as described above on the inner surface of template halves 90 and 92, which may be made from nonconductive material. Pressure or compression is applied to the cartilage by means of template halves 90 and 92 while current or electric field is formed between dot electrodes 84. Conventional printed circuit board wiring can be fabricated in template halves 90 and 92 for electrical connections to dot electrodes 84.

Figure 14A:
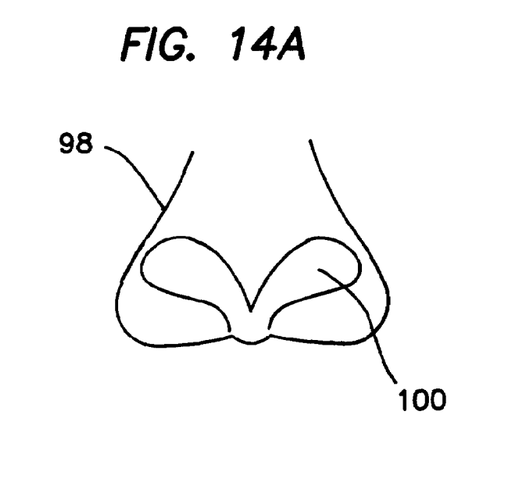
FIGS. 14a and 14b are diagrams showing the anatomical position of cartilage in the tip of the nose in a front plan view and side view respectively.
Figure 14B:
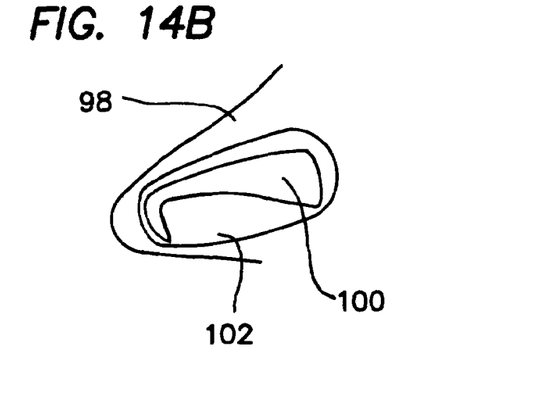

FIGS. 14a and 14b show a front plan view and a side view respectively of the cartilage anatomy 100 in a typical human nose 98. In FIG. 14b a curved or flat plate 102 is depicted which is slid over and overlaps cartilage 100. An identical plate would be surgically disposed on the opposing side of cartilage 100. Plates 102 would be provided with electrode arrays such as described in connection with FIGS. 12a-12d. Pressure could be applied directly by tongs to opposing plates 102 or simply provided to the outside of the nasal tissues and indirectly transmitted to plates 102 and hence to cartilage 100.

Figure 15A:
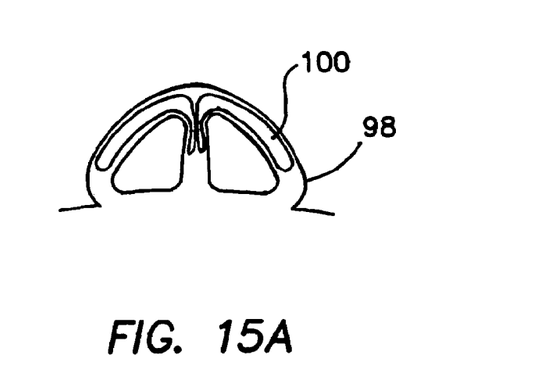
Figure 15B:
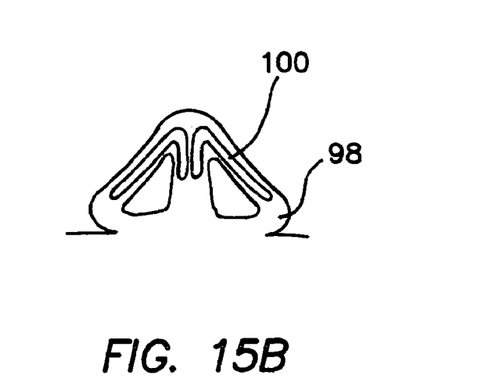
Figure 15C:
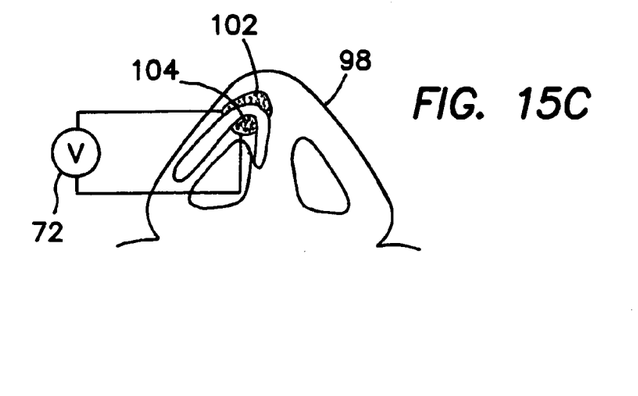

FIGS. 15a and 15b show a bottom plan view looking upwardly of the cartilage anatomy 100 in a typical human nose 98. FIG. 15a shows the beginning anatomy of the medial and lateral cura, where the tip of the nose is bulbous or rounded in section due to the underlying cura shape. FIG. 15b shows the same nose 98 after the medial and lateral cura of cartilage 100 has been more acutely electroformed to give a pointed nose tip shape. This is accomplished by means of a pair of shaped jigs 102 and 104 carrying electrodes or acting as electrodes and coupled to voltage source 72. Incisions are made into the base of nose 98 and jigs 102 and 104 are slide into place on each side of the cura. Jigs 102 and 104 are directly or indirectly squeezed together to apply stress or compression to the cura as current or voltage is applied to jigs 102 and 104.

Figure 16A:
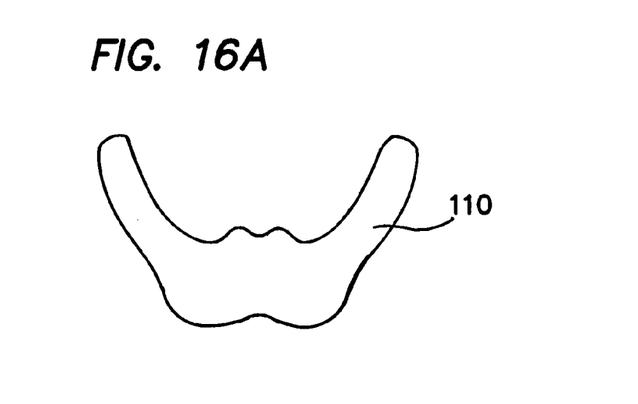
FIG. 16a is a front plan view of the thyroid cartilage.
Figure 16B:
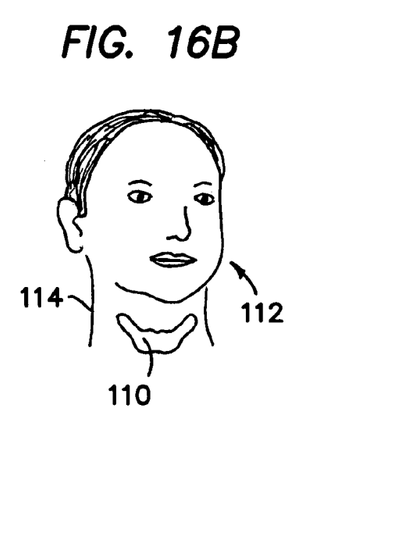
FIG. 16b is a front plan view which illustrates it anatomical position in the neck or throat.
Figure 16C:
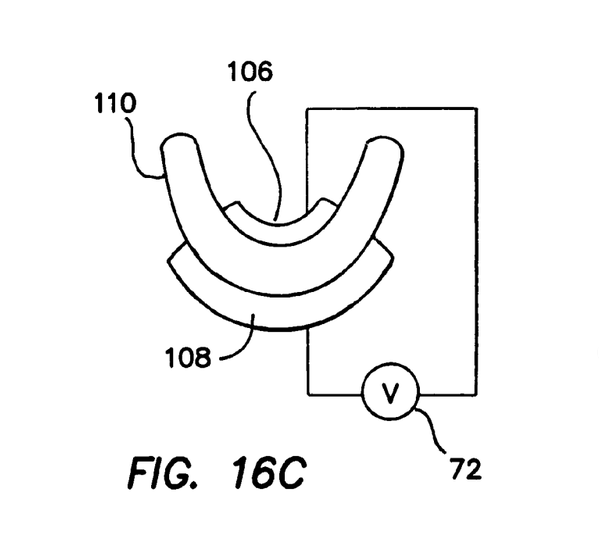
FIG. 16c is a top cross sectional view of the thyroid cartilage undergoing treatment.
Figure 16D:
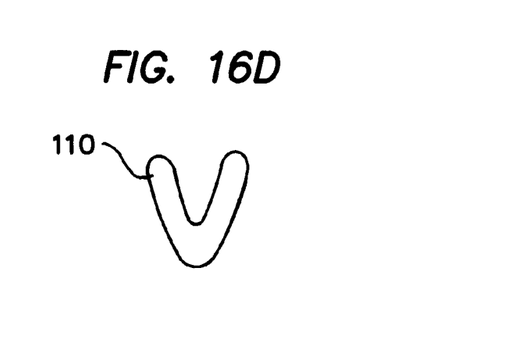
FIG. 16d is a top cross sectional view of the thyroid cartilage after being treated to be more acutely curved.
Figure 16E:
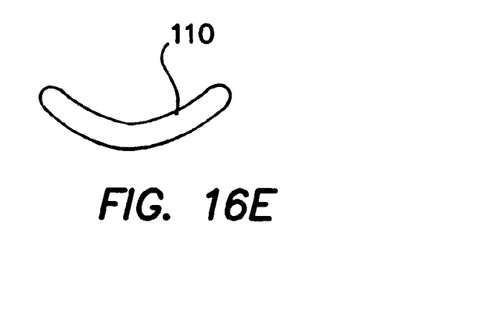
FIG. 16e is a top cross sectional view of the thyroid cartilage after being treated to be more obtusely curved.

FIGS. 16a-16e illustrate the application of the invention to the thyroid cartilage 110 shown in front plan view in FIG. 16a. The thyroid cartilage 110 is positioned in the neck 114 of a patient 112 in front of the voice box as shown in FIG. 16b. A jig 106 can be implanted endoscopically through the throat to the interior surface of thyroid cartilage 110 as shown in the top cross sectional view of FIG. 16c. A jig 108 can be implanted percutaneously or endoscopically to the exterior surface of thyroid cartilage 110 as shown in the top cross sectional view of FIG. 16c. Again jigs 106 and 108 can be made from nonconducting material and provided with any one of the style of electrodes shown in FIGS. 12a-12d or any equivalent electrode means. The result, for example, may be a more acutely curved thyroid cartilage 110 as shown in the top cross sectional view of FIG. 16d or a more obtusely curved thyroid cartilage 110 as shown in the top cross sectional view of FIG. 16e depending the shapes of jigs 106 and 108.

It must be understood that the method of the invention may be practiced for a predetermined operative time measured in minutes to a few hours after which the electrodes or jigs are removed, or may be included in an implantable device and worn by the patient for days or months while the electroforming is continuously or periodically being applied using a portable voltage source and controller.

Further, it must be understood that while the mechanism of electroforming is not perfectly understood, it is only necessary to place a stress on the tissue or cartilage while a current or electric field is impressed on the tissue or cartilage. For example, it may be enough that only an electric field need be presented while the tissue or cartilage is being stressed and that no actual current need be conducted through the tissue or cartilage or direct electrode contact with the tissue or cartilage be made.

In summary, we disclose a novel method of reshaping cartilage. This is the first documentation that describes a nonthermal, electrically-mediated technique to reshape cartilage. Our selective measurement of the change in shape, temperature, and surface features creates a solid foundation for future studies of electroforming.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus of electroforming tissue to reshape the tissue comprising:
    means for creating stress in the tissue to temporarily define and maintain a predetermined shape of the tissue;
    means for monitoring the stresses in the tissue comprises a means for monitoring the color of the tissue as caused by electroplating a material thereon;
    means for causing a direct current of a predetermined polarity to flow in the tissue to mediate the tissue while the created stress is present to permanently change shape of the tissue or material parameters of the tissue without necrosis or ablation; and
    means for controlling the direct current flowing in the tissue according to the stresses therein.

2. An apparatus of electroforming tissue to reshape the tissue comprising:
    means for creating stress in the tissue to temporarily define and maintain a predetermined shape of the tissue;
    means for causing a direct current of a predetermined polarity to flow in the tissue comprises means for applying voltage pulses of the same polarity to form a DC pulse train to mediate the tissue while the created stress is present to permanently change shape of the tissue or material parameters of the tissue without necrosis or ablation; and
    means for applying a voltage of predetermined polarity to obtain a predetermined bioeffect comprises means for applying a first sequence of voltage pulses of the same polarity and means for applying a second sequence of voltage pulses of the opposite polarity to form a complex DC pulse train.

3. An apparatus of electroforming tissue to reshape the tissue comprising:
    means for creating stress in the tissue to temporarily define and maintain a predetermined shape of the tissue;
    means for causing a direct current of a predetermined polarity to flow in the tissue comprises means for applying voltage pulses of the same polarity to form a DC pulse train to mediate the tissue while the created stress is present to permanently change shape of the tissue or material parameters of the tissue without necrosis or ablation;
    means for applying a voltage of predetermined polarity to obtain a predetermined bioeffect comprises means for applying a first sequence of voltage pulses of the same polarity and means for applying a second sequence of voltage pulses of the opposite polarity to form a complex DC pulse train; and
    means for applying a first sequence and means for applying a second sequence of voltage pulses provide a net charge cancellation when integrated over an application time.

* * * * *